United States Patent
Costall

Patent Number: 5,177,086
Date of Patent: Jan. 5, 1993

[54] MEMORY-ENHANCING COMPOSITIONS CONTAINING DIOXOPIPERIDINE DERIVATIVES

[75] Inventor: Brenda Costall, Addingham, United Kingdom

[73] Assignee: National Research Development Corporation, London, England

[21] Appl. No.: 729,851

[22] Filed: Jul. 12, 1991

Related U.S. Application Data

[63] Continuation of Ser. No. 433,614, Nov. 9, 1989, abandoned.

[30] Foreign Application Priority Data

Nov. 10, 1988 [GB] United Kingdom ............ 8826308

[51] Int. Cl.⁵ .......................................... A01N 43/40
[52] U.S. Cl. ............................................... 514/328
[58] Field of Search .................................... 514/328

[56] References Cited

U.S. PATENT DOCUMENTS

| | | | |
|---|---|---|---|
| 4,705,796 | 11/1987 | Hendry et al. | 514/328 |
| 4,738,973 | 4/1988 | Gittos | 514/328 |
| 4,835,151 | 5/1989 | Gittos | 514/219 |
| 4,871,750 | 10/1989 | Roberts | 514/328 |
| 4,877,800 | 10/1989 | Costall | 514/328 |

FOREIGN PATENT DOCUMENTS 2181346 4/1987 United Kingdom .

*Primary Examiner*—Frederick E. Waddell
*Assistant Examiner*—T. J. Criares
*Attorney, Agent, or Firm*—Cushman, Darby & Cushman

[57] ABSTRACT

Phenyl-3-aminoalkyl-4-methyl-2,6-dioxopiperidines of the Formula I

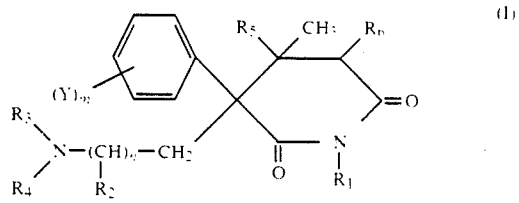

wherein:
- $R_1$ represents hydrogen or $C_1$–$C_4$ alkyl;
- n is 1 or 2;
- $R_2$ represents hydrogen or methyl, provided that one $R_2$ is hydrogen when n is 2;
- $R_3$ represents hydrogen or $C_1$–$C_2$ alkyl;
- $R_4$ represents $C_1$–$C_2$ alkyl;
- $R_5$ and $R_6$ independently represent hydrogen or methyl;
- m is 0 to 3; and
- each Y is in a meta or para position and independently represents hydroxy, $C_1$–$C_2$ alkoxy, $C_1$–$C_2$ alkyl, $C_1$–$C_2$ hydroxyalkyl, halogen, or trifluoromethyl, provided that hydroxy and alkoxy are not in the para position.

and not pharmacologically acceptable salts thereof have memory enhancing activity and are particularly useful in the treatment of cognitive deficiencies such as senile dementia.

The presently preferred compound is 3-(3'methoxyphenyl)-3-(3'-N,N-dimethylaminopropyl)-4,4-dimethyl-2,6-dioxopiperidine (AGN 2979).

9 Claims, 5 Drawing Sheets

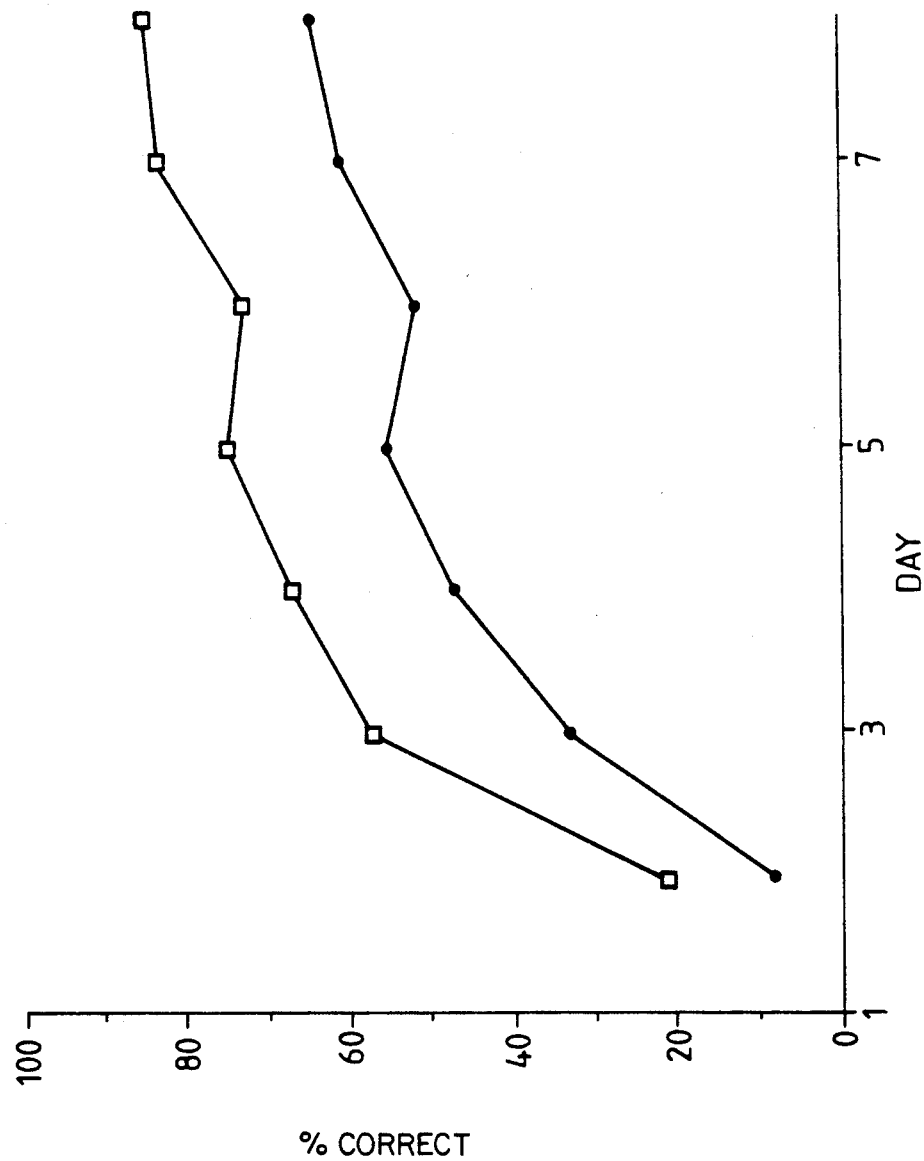

MEMORY-ENHANCING COMPOSITIONS CONTAINING DIOXOPIPERIDINE DERIVATIVES

This is a continuation of application Ser. No. 07/433,614, filed on Nov. 9, 1989, which was abandoned upon the filing hereof.

This invention relates to the use of certain 3-phenyl-3-aminoalkyl-4-methyl-2,6-dioxopiperidines to enhance memory especially in patients suffering cognitive deficiencies. In particular, the invention provides the use of the said dioxopiperidines in the manufacture of medicaments to enhance memory and/or treat cognitive deficiencies and methods of enhancing memory and/or treatment of cognitive deficiencies using said dioxopiperidines.

Cognition is the neurological process by which knowledge is acquired and involves the ability of the brain to store and recall information (i.e. memory). Old age and various neurological conditions produce detrimental cognitive effects. Such effects are particularly significant in senile dementia of Alzheimer's disease, Parkinson's disease, Huntingdon's chorea, ischaemia, stroke, alcoholism, and drug abuse, and in some childhood attentional problems.

It has surprisingly now been found that certain 3-phenyl-3-aminoalkyl-4-methyl-2,6-dioxopiperidines (as defined hereinafter) are effective in the treatment of cognitive deficiencies and, more generally, enhance memory.

GB 1455687 (also AU 480855 BE 808958, DE 23630526, FR 7346904, JP 6053014 and US 3963729) discloses that 3-phenyl-3-aminoalkyl-4- and/or 5-methyl-2,6-dioxopiperidine derivatives have central nervous system, especially antidepressant, activity. Said compounds include, inter alia, those of the following Formula A.

It also has been disclosed in U.S. Pat. No. 4,461,771 that compounds of Formula A, in which $R_1$ represents hydrogen; $R_3$ and $R_4$ independently represent methyl or ethyl; $R_5$ represents methyl; $R_6$ represents hydrogen; A represents ethylene or propylene; m is 1 or 2, and each Y is in a meta position and independently represents hydroxy or $C_1$-$C_2$ alkoxy, are believed to reduce in vitro the activity of tryptophan hydroxylase by blocking the depolarization-induced activation of the enzyme in the brain stem and hence are of potential use in the prophylactic treatment of the stressful disorder migraine. More recently, it has been reported that at least one compound of Formula A (viz 3-(3'-methoxyphenyl)-3-(3''-N,N-dimethylaminopropyl)-4,4-dimethyl-2,6-dioxo-piperidine; AGN 2979) also blocks in vitro the activation of tryptophan hydroxylase resulting from exposure of brain stem slices to metabolic inhibitors or methylxanthines or induced by incubation of supernatant preparations of the enzyme under phosphorylating conditions (Boadle-Biber, M.C. et al Biochem. Pharmacol. 35, 1521–6, (1986)). However, it also has been reported that AGN 2979 has no significant effect in vitro upon the unactivated enzyme (Boadle-Biber, M.C. et al supra).

Further, it has recently been disclosed in GB 2181346A that compounds of Formula A, in which $R_1$ represents hydrogen; $R_3$ and $R_4$ independently represent methyl or ethyl; A represents ethylene or propylene; m is 1 or 2; and each Y is in a meta position and independently represents hydroxy or $C_1$-$C_2$ alkoxy, are believed to reduce the turnover of 5-hydroxytryptamine (5HT) resulting from inhibiting the activity of tryptophan hydroxylase. They are reported to have anxiolytic activity, antagonize the anxiogenic activity of benzodiazepines inverse agonists, reduce chronic abnormally high brain levels of 5HT or its metabolite 5-hydroxy-indoleacetic acid, and have antibacterial and antiviral activity.

According to a first aspect of the present invention, there is provided the use in the manufacture of a medicament for the treatment of cognitive deficiencies or for the enhancement of memory of a compound of the following Formula I.

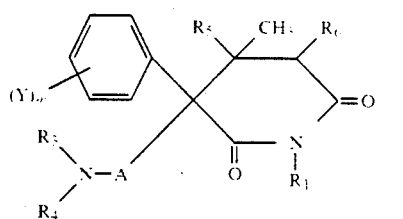
(A)

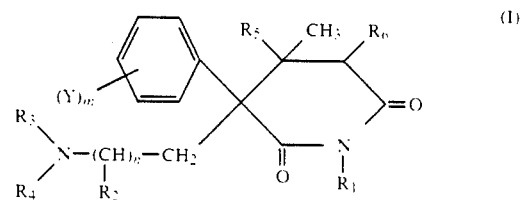
(I)

wherein:
$R_1$ represents hydrogen or $C_1$-$C_4$ alkyl;
$R_3$ represents hydrogen or $C_1$-$C_4$ alkyl;
$R_4$ represents $C_1$-$C_4$ alkyl;
$R_5$ and $R_6$ independently represent hydrogen or methyl;
A represents $C_1$-$C_6$ alkylene;
m is 0 to 3; and
Y is hydroxy, $C_1$-$C_4$ alkoxy, $C_1$-$C_4$ alkyl, $C_1$-$C_4$ hydroxyalkyl, halogen or trifluoromethyl.

wherein:
$R_1$ represents hydrogen or $C_1$-$C_4$ alkyl;
n is 1 or 2;
$R_2$ represents hydrogen or methyl, provided that one $R_2$ is hydrogen when n is 2;
$R_3$ represents hydrogen or $C_1$-$C_2$ alkyl;
$R_4$ represents $C_1$-$C_2$ alkyl;
$R_5$ and $R_6$ independently represent hydrogen or methyl;
m is 0 to 3 and
each Y is in a meta or para position and independently represents hydroxy, $C_1$-$C_2$ alkoxy, $C_1$-$C_2$ alkyl, $C_1$-$C_2$ hydroxyalkyl, halogen, or trifluoromethyl, provided that hydroxy and alkoxy are not in the para position, or a pharmacologically acceptable salt thereof.

In a second aspect, the invention provides a method of enhancing memory or treating a patient suffering from cognitive deficiency, which comprises administering to the patient a memory enhancing effective amount of a compound of the following Formula I.

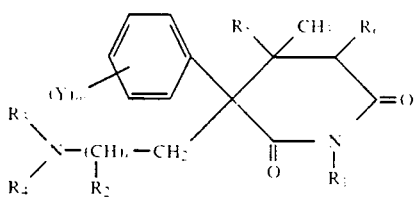

(I)

wherein:
$R_1$ represents hydrogen or $C_1$-$C_4$ alkyl;
n is 1 or 2;
$R_2$ represents hydrogen or methyl, provided that one $R_2$ is hydrogen when n is 2;
$R_3$ represents hydrogen or $C_1$-$C_2$ alkyl;
$R_4$ represents $C_1$-$C_2$ alkyl;
$R_5$ and $R_6$ independently represent hydrogen or methyl;
m is 0 to 3; and
each Y is in a meta or para position and independently represents hydroxy, $C_1$-$C_2$ alkoxy, $C_1$-$C_2$ alkyl, $C_1$-$C_2$ hydroxyalkyl, halogen, or trifluoromethyl, provided that hydroxy and alkoxy are not in the para position,
or a pharmacologically acceptable salt thereof.

The compounds of Formula I can be prepared in the manner disclosed in GB 1455687. They exist as optical isomers and can be used in racemate form or as individual (+) or (−) isomers. Presently, the (−) isomer is preferred.

The compounds of Formula I can be administered in various manners to achieve the desired memory enhancing effect. The compounds can be administered enterally or parenterally to the patient being treated. Oral administration is likely to be the preferred route in most circumstances but injection, especially subcutaneously or intravenously, will be preferred in some circumstances.

The amount of compound administered will vary and can be any memory enhancing effective amount. Depending upon the patient and the mode of administration, the amount of compound administered may vary over a wide range to provide from about $10^{-7}$ to $10^2$ mg/kg, usually $10^{-5}$ to $10^2$ mg/kg, especially $10^{-4}$ to $10^2$ mg/kg of body weight of the patient per unit dose. Unit doses of these compounds can contain, for example, from about $10^{-6}$ mg to 500 mg, usually $10^{-4}$ to $10^2$ mg, especially $10^{-3}$ to $10^2$ mg of the compound and may be administered, for example, from 1 to 4 times daily.

The term "unit dosage form" is used herein to mean a single or multiple dose form containing a quantity of the active ingredient in admixture with or otherwise in association with a diluent or carrier, said quantity being such that one or more predetermined units are normally required for a single therapeutic administration. In the case of multiple dose forms such as liquids or scored tablets, said predetermined unit will be one fraction, such as a 5 ml (teaspoon) quantity of a liquid or a half or quarter of a scored tablet, of the multiple dose form.

The compounds of general Formula I can have the phenyl moiety substituted in one or both meta positions by $C_1$-$C_2$ alkyl, $C_1$-$C_2$ hydroxyalkyl, halogen, trifluoromethyl, or, preferably, hydroxy or $C_1$-$C_2$ alkoxy. Additionally or alternatively, the phenyl moiety can be substituted in the para position by the aforementioned groups other than hydroxy and alkoxy. It is presently preferred that the substituent(s) should be hydroxy or, especially, methoxy. It is also preferred that one or both meta positions are substituted and that, when there are two substituents, they should be the same.

The amino group of the compounds of Formula I can be secondary or tertiary having methyl or ethyl groups attached to the nitrogen atom. Dimethylamino presently is preferred. The amino group is connected to the piperidine ring by a divalent ethylene (i.e. n=1) or trimethylene (i.e. n=2) radical optionally substituted on a carbon atom not adjacent said ring with a methyl group. Presently, unsubstituted trimethylene is preferred.

The piperidine ring of the compounds of Formula I is substituted in the 4-position with methyl and optionally by one or two further methyl groups in the 4 and/or 5 positions. It is presently preferred that there is one further methyl group in the 4 or 5 position, especially in the 4-position.

The ring nitrogen atom of the piperidine ring can be substituted with a $C_1$-$C_4$ alkyl group but it is presently preferred that said nitrogen atom is unsubstituted.

The $C_1$-$C_2$ alkyl groups or moieties referred to herein are methyl or ethyl; methyl presently being preferred. The $C_3$-$C_4$ alkyl groups which may be substituents on the nitrogen atom of the piperidine ring can be straight or branched chain but the straight chain n-propyl or n-butyl groups presently are preferred. The halogen substituent(s) in the phenyl ring can be chlorine, bromine or fluorine, chlorine presently being preferred.

The presently preferred compounds of Formula I are those of the following Formula IA.

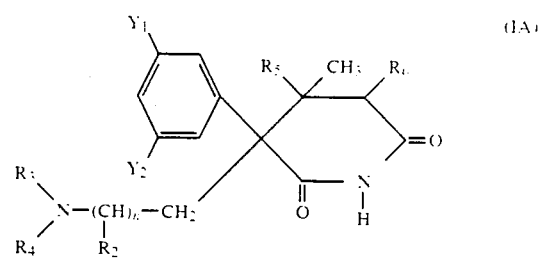

(IA)

wherein:
n is 1 or 2;
$R_2$ represents hydrogen or methyl, provided that one $R_2$ is hydrogen when n is 2;
$R_3$ represents hydrogen or $C_1$-$C_2$ alkyl;
$R_4$ represents $C_1$-$C_2$ alkyl;
$R_5$ and $R_6$ independently represent hydrogen or methyl; and
$Y_1$ and $Y_2$ independently represent hydrogen, hydroxy or $C_1$-$C_2$ alkoxy,
or a pharmacologically acceptable salt thereof.

The presently especially preferred compounds of Formula IA are those of the following Formula IB.

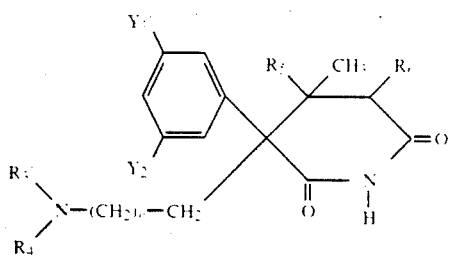

(IB)

wherein :
n is 1 or 2;
$R_3'$ and $R_4$ independently represent $C_1-C_2$ alkyl;
$R_5$ and $R_6$ independently represent hydrogen or methyl;
$Y_1'$ represents hydroxy or $C_1-C_2$ alkoxy; and
$Y_2'$ represents hydrogen, hydroxy or $C_1-C_2$ alkoxy, or a pharmacologically acceptable salt thereof.

BRIEF DESCRIPTION OF THE DRAWINGS

Further objects and advantages of the present invention will be better understood by carefully reading the present description of the invention in conjunction with the accompanying drawings, of which:

FIG. 4 shows the effect of age on choice performance relating to the T-maze test results of Example 7.

Figure 1A:
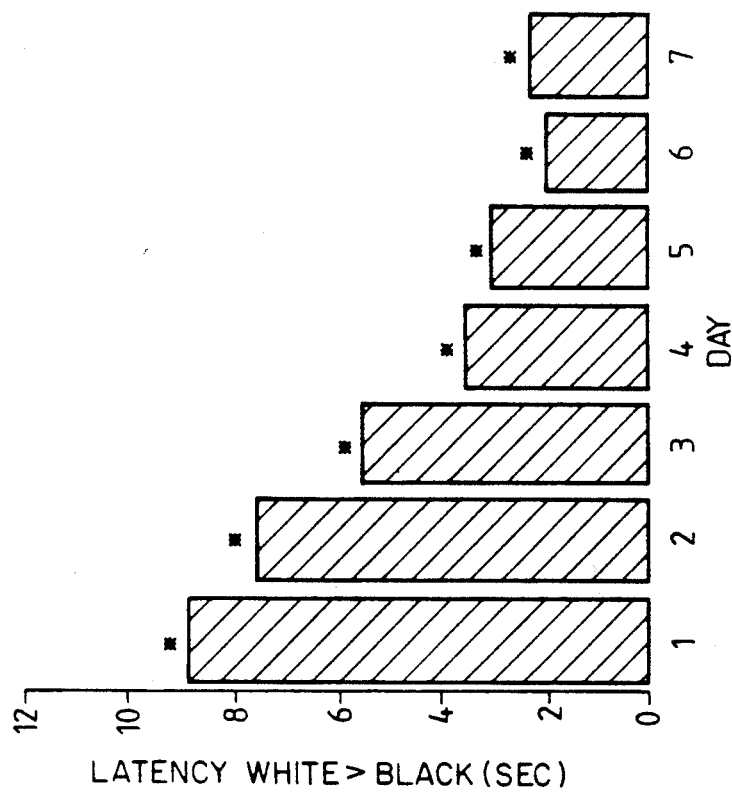
FIG. 1A and FIG. 1B present results from the mouse habituation test of Example 6.
Figure 1B:
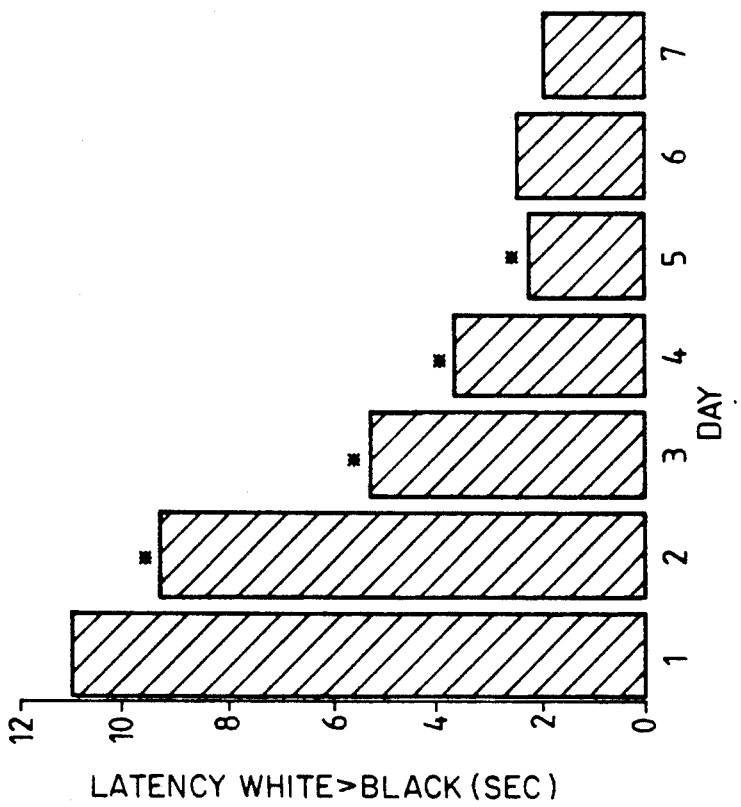
Figure 2A:
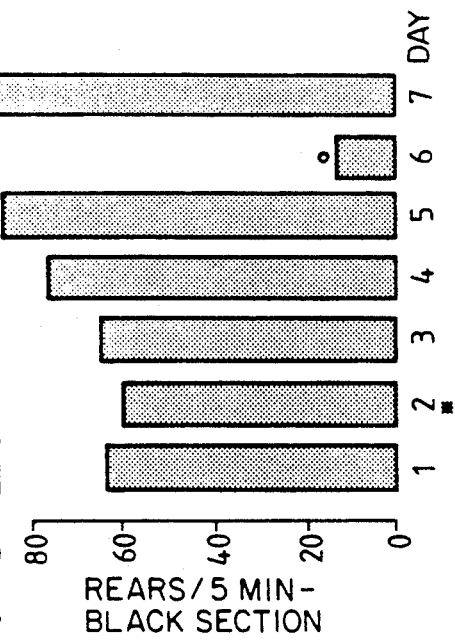
FIG. 2A, 2B, 2C and FIG. 2D present results of the mouse habituation test in Example 6.
Figure 2C:
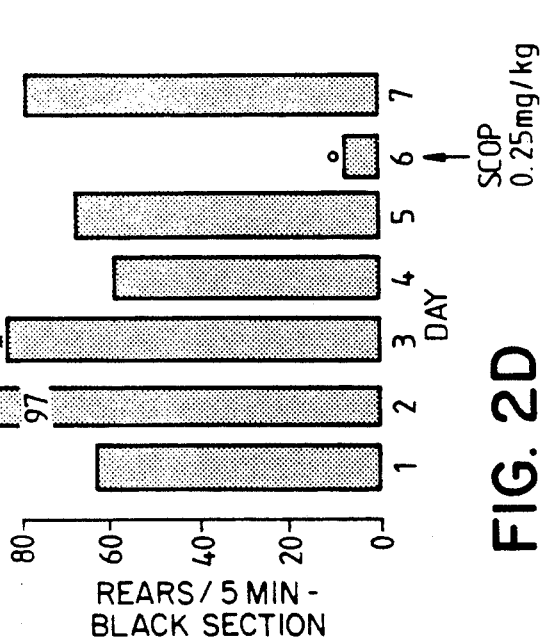
Figure 2B:
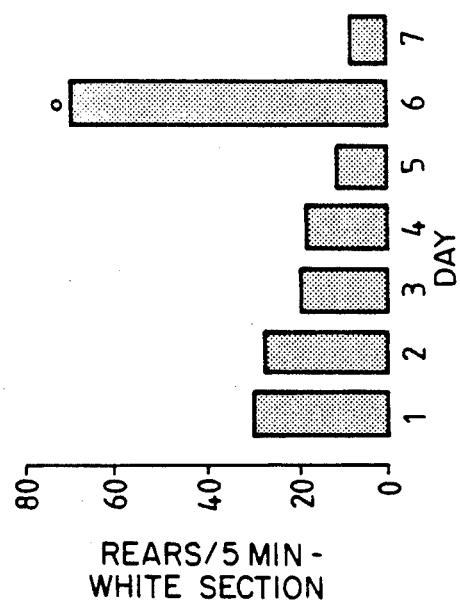
Figure 2D:
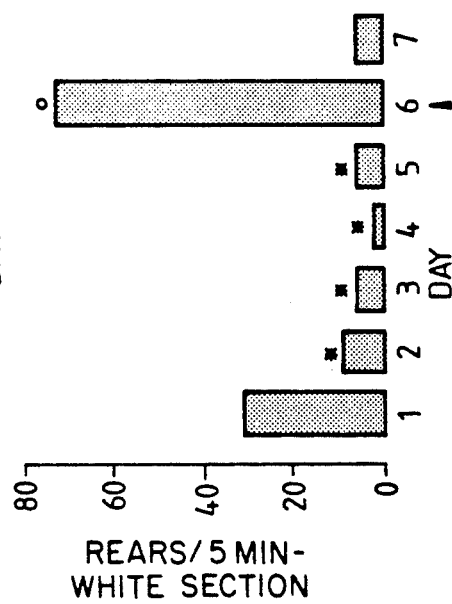
Figure 3A:
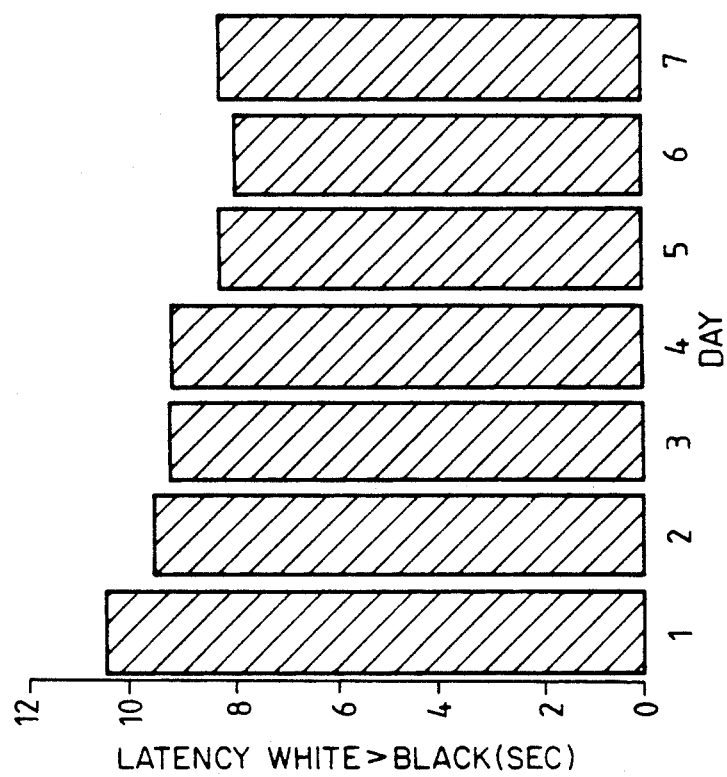
FIG. 3A and FIG. 3B show a comparison of habituation profiles of young adults and aged mice, related to Example 6.
Figure 3B:
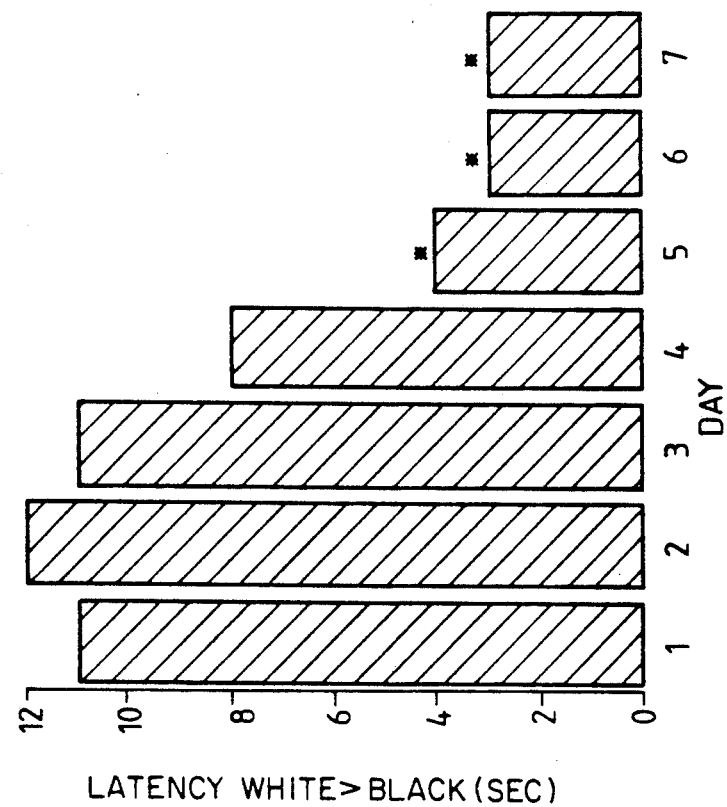
Figure 5:
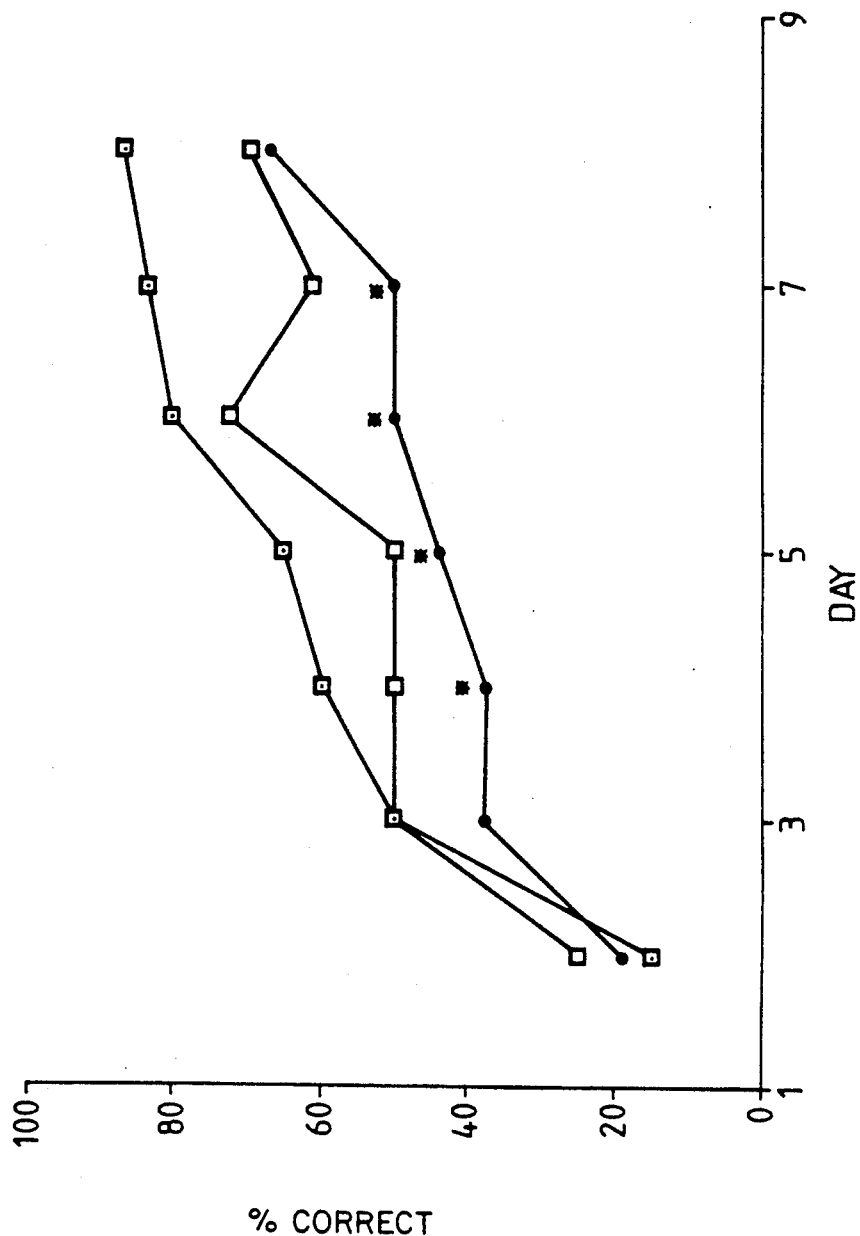
FIG. 5 shows results relating to the T-maze test of Example 7.

Examples of compounds of Formula IB include the following:

3-(3'-methoxyphenyl)-3-(2"-N,N-dimethylaminoethyl)-4,4-dimethyl-2,6-dioxopiperidine 3-(3'-methoxyphenyl)-3-(3"-N,N-dimethylaminopropyl)-4,4-dimethyl-2,6-dioxopiperidine (AGN 2979);

3-(3'-methoxyphenyl)-3-(2"-N,N-diethylaminoethyl)-4,4-dimethyl-2,6-dioxopiperidine;

3-(3'-methoxyphenyl)-3-(3"-N,N-diethylaminopropyl)-4,4-dimethyl-2,6-dioxopiperidine;

3-(3'-hydroxyphenyl)-3-(2"-N,N-dimethylaminoethyl)-4,4-dimethyl-2,6-dioxopiperidine;

3-(3'-hydroxyphenyl)-3-(3"-N,N-dimethylaminopropyl)-4,4-dimethyl-2,6-dioxopiperidine;

3-(3'-methoxyphenyl)-3-(2"-N,N-dimethylaminoethyl)-4,5-dimethyl-2,6-dioxopiperidine (AGN 2939);

3-(3'-methoxyphenyl)-3-(3"-N,N-dimethylaminopropyl)-4,5-dimethyl-2,6-dioxopiperidine (AGN 3181);

3-(3'-ethoxyphenyl)-3-(3"-N,N-dimethylaminopropyl)-4,4-dimethyl-2,6-dioxopiperidine;

3-(3'-ethoxyphenyl)-3-(3"-N,N-diethylaminopropyl)-4,4-dimethyl-2,6-dioxopiperidine;

3-(3',5'-dimethoxyphenyl)-3-(3"-N,N-dimethylaminopropyl)-4,4-dimethyl-2,6-dioxopiperidine (AGN 3222);

3-(3',5'-dimethoxyphenyl)-3-(2"-N,N-dimethylaminoethyl)-4,4-dimethyl-2,6-dioxopiperidine;

3-(3',5'-dimethoxy phenyl)-3-(3"-N,N-dimethylaminopropyl)-4,5-dimethyl-2,6-dioxopiperidine; and 3-(3',5'-dimethoxyphenyl)-3-(2"-N,N-dimethylaminoethyl)-4,5-dimethyl-2,6-dioxopiperidine;

Examples of other compounds of Formula I include 3-phenyl-3-(2'-N,N-dimethylaminoethyl)-4-methyl-2,6-dioxopiperidine;

3-phenyl-3-(2'-N,N-dimethylaminoethyl)-4,4-dimethyl-2,6-dioxopiperidine;

3-phenyl-3-(2'-N,N-dimethylaminoethyl)-4,5-dimethyl-2,6-dioxopiperidine;

3-phenyl-3-(3'-N,N-dimethylaminopropyl)-4,4-dimethyl-2,6-dioxopiperidine;

3-(4'-chlorophenyl)-3(3"-N,N-dimethylaminopropyl)-4,4-dimethyl-2,6-dioxopiperidine; and 3-phenyl-3(2'N-methylaminoethyl)-4,4-dimethyl-2,6-dioxopiperidine.

The compounds of Formula I may be administered in free base form, as an alkali metal or alkaline earth metal salt or as a pharmaceutically acceptable acid addition salt with the proviso that an alkali metal or alkaline earth metal salt is not normally combined with an acid addition salt except in a layer formulation. Representative acid addition salt forms include organic acid salt forms such as the maleate and methane sulphonate and mineral acid salt forms such as the hydrochloride and perchlorate.

The pharmaceutical formulations in which form the active compounds of the invention will normally be utilized are prepared in a manner well known per se in the pharmaceutical art and usually comprise at least one active compound of Formula I in admixture or otherwise in association with a pharmaceutically acceptable carrier or diluent therefor. For making those formulations the active ingredient will usually be mixed with a carrier, or diluted by a diluent, or enclosed or encapsulated in a capsule, sachet, cachet, paper or other container. A carrier or diluent may be solid, semi-solid or liquid material which serves as a vehicle, excipient or medium for the active ingredient. Suitable carriers or diluents are well known per se.

The formulations may be adapted for enteral or parenteral use and may be administered to the patient in the form of tablets, capsules, dragees, suppositories, syrups, suspensions, subcutaneous or intransmuscular depot injections or implants or the like. The formulations may be in delayed or sustained release form.

Aside from the active agents the compositions may contain pharmaceutically inert organic or inorganic adjuvants, optionally granulating agents, binding agents lubricants, dispersing agents, wetting agents and preservatives. Moreover, the pharmaceutical compositions may contain colouring, flavouring and sweetening substances. Adjuvants for the production of tablets may be e.g. calcium carbonate, lactose micro-crystalline cellulose, mannitol or talc. Starch and alginic acid or microcrystalline cellulose may be used as granulating and disintegrating agents, starch, polyvinylpyrrolidone and gelatine may be used as binding agents and magnesium stearate, stearic acid, colloidal silica and talc as lubricants. Tablet formulation may be coated or uncoated, the coating having the purpose of delaying the disintegration and absorption in the gastrointestinal tract. Suitable suspending agents for the production of liquid administration forms are e.g. methyl cellulose and sodium alginate. Capsule formulation may contain the active agents on their own or together with an inert solid diluent e.g. calcium phosphate, corn starch, lactose, or mannitol.

The invention is illustrated in the following non-limiting Examples.

EXAMPLE 1

Tablet Formulation

Tablets each having the following composition are prepared by conventional techniques:

|     |                      | mg/tablet |
| --- | -------------------- | --------- |
| (a) | Compound AGN 2979 base | 1       |
| (b) | Lactose              | 51.5      |
| (c) | Maize starch dried   | 45        |
| (d) | Magnesium stearate   | 1.5       |

EXAMPLE 2

Suppository Formulation

|     |                              | mg/suppository |
| --- | ---------------------------- | -------------- |
| (a) | Compound AGN 2979 HCl        | 10             |
| (b) | Oil of Theobroma (cocoa butter) | 990         |

The compound (a) is powdered and passed through a BS No. 100 sieve (150 micrometres) and triturated with molten oil of Theobroma at 45° C. to form a smooth suspension. The mixture is well stirred and poured into moulds each of nominal 1 G capacity to produce suppositories.

EXAMPLE 3

Tablet Formulation

|     |                          |        |
| --- | ------------------------ | ------ |
| (a) | Compound AGN 2979 base   | 10 mg  |
| (b) | Wheat starch             | 7 g    |
| (c) | Lactose                  | 20 g   |
| (d) | Magnesium Stearate       | 1 g    |

EXAMPLE 4

Pill Formulation

|     |                       | per pill |
| --- | --------------------- | -------- |
| (a) | Compound AGN 2979 HCl | 10 mg    |
| (b) | Corn starch           | 45 mg    |
| (c) | Liquid glucose        | 7 ml     |

The pills are prepared by blending the active ingredient (a) and the corn starch, then adding the liquid glucose with thorough kneading to form a plastic mass from which the pills are cut and formed.

EXAMPLE 5

Gelatine Capsule Formulation

|     |                       | per capsule |
| --- | --------------------- | ----------- |
| (a) | Compound AGN 2979 HCl | 2.5 mg      |
| (b) | Talc                  | 70 mg       |

A capsule is prepared by passing dry powdered active ingredient (a) and powdered talc in the above proportions through a fine mesh screen and mixing them well. The powder is then filled into hard gelatin capsules at a net fill of 72.5 mg per capsule.

EXAMPLE 6

Mouse Habituation Test

The studies used male albino (BKW) mice initially weighing 25-30 g (young 6-8 weeks) or 30-35 g (9 months). In their home room mice were housed in groups of 10 and were given free access to food and water. The mice were kept on a 12h light and 12h dark cycle with lights off at 8.00 am and on at 8.00 pm.

The test apparatus consisted of an open-topped box (45×27×27 cm) one third painted black and illuminated under a dim red light (1×60 W) and partitioned from the remainder of the box which was brightly illuminated with a 100 W light source located 17 cm above the box. Access between these two areas was enabled by means of a 7.5×7.5 cm opening located at floor level in the centre of the partition (which also served to prevent diffusion of light between the two compartments of the test box). The floor area was lined into 9 cm squares.

The habituation test was carried out daily by placing mice in the centre of the white section of the test box (mice taken from dark home environment in a dark container, to the experimental room maintained in low red lighting, and would normally be averse to the bright white conditions). Testing was carried out between 8.30 am and 12.30 pm. The test period was 5 min per day. Behaviour was assessed via remote video recording, and the following measures taken:

1. Latency to move from the white to the black section (sec).
2. Numbers of exploratory rears in the white and black sections during the 5 min tests.
3. Numbers of line crossings (exploratory locomotion) in the white and black sections during the 5 min test.
4. % Time spent in the black section of the box during the 5 min test.
5. Numbers of transitions between the black and white sections of the test box during the 5 min test (since this parameter was not changed in any situation in the present studies, data for transitions is not given or commented on further).

On repeated daily exposure to the box young adult mice habituate to the test situation by moving rapidly into the black area where they spend most time and exhibit most behaviour (measured as exploratory rears and crossings of lines marked on the test box floor). Generally, for young adult mice the habituation process occurs over a 4-6 day period and, for example, latency for the initial movement from the white to the black section is reduced from initial values of 10-12 sec to 1-4 sec by the 5th-6th day of test.

In the contrast to the findings with young adult mice (6-8 weeks old), aged mice (9 months old) fail to habituate to the black:white test system. From the first day of test aged animals' behaviour appears to be equally distributed between the white and black sections, and expected changes in behaviour to favour the preferred black environment do not occur.

The habituation profile of young mice was disrupted by acute scopolamine (0.25 mg/kg i.p., 40 min before test) (dose carefully selected as minimally effective, without interference from peripheral effects as checked by assessments of the actions of the same dose of methylscopolamine). Aged mice were found to be particularly sensitive to scopolamine and they were challenged with the maximally tolerated dose of 0.1 mg/kg (40 min before test).

AGN 2979 was given i.p. b.d. throughout the habituation period (dose of 0.001 mg/kg selected as not interferring with anxiety responding). Injections of AGN 2979 were at 8.00 am and 8.00 pm.

AGN 2979 improved basal performance in both young adult and aged mice. but did not prevent the detriments caused by scopolamine.

The results are set forth in FIGS. I to III.

EXAMPLE 7

Food Reinforced Alternation Task in Rat Using an Elevated T-Maze

The studies used male Lister hooded rats initially weighing 300-359 g (young adult 11-15 weeks) or 380-450 g (aged 13-17 months). Rats were normally housed in groups of 5 in a room maintained at $22° \pm 1°$ C., on a 12h light:dark cycle with lights on at 8.00 am and off at 8.00 pm. The test room was maintained under identical conditions. and was sound-proofed.

The apparatus and technique used was essentially that of Salamone et al. (Behav. Brain Res. 13, 63-70, 1984) using a T-maze constructed of wood and elevated 30 cm from the ground with side arms measuring 60 cm × 10 cm and start arm measuring 80 cm × 10 cm. A small metal cup was placed towards the end of each side arm; these held the reward pellets as appropriate. A line was marked 20 cm from the start of each side arm.

Animals were food deprived excepting for 1 hr posttest, for 2 days prior to testing and throughout the 9 day test period, but water was available ad libitum. Animals maintained 85% of normal body weight throughout testing. A few banana-flavoured reward pellets were mixed with the food to habituate the rats to the taste of the pellets. The rats showed clear preference for banana-flavoured pellets as compared with their normal laboratory chow.

Rats were allowed 10 min habituation to the T-maze on day 1 (both arms baited with banana-flavoured reward pellets, 4 × 45 mg pellets in each cup) and were subject to a pretraining period of reinforced alternation on days 2-5 of test, with training on days 6-9. All training consisted of paired trials (each constituting a "run"), the first being "forced" in that one arm was blocked with a wooden barrier whilst the other was baited (for a positive response on the forced trial the rat must take the food). The second was a "choice" trial in which reward pellets were placed in the arm opposite to that reinforced on the first trial of the pair. A correct choice was when the rat entered the arm containing the food on the choice trial, crossing the point marked 20 cm from the start of the side arm.

In addition to correct/incorrect choice, latency to reward was recorded for both forced and choice trials. 4 runs/day were carried out on pretraining days (inter-trial interval 0 sec, inter-run interval 30 sec), 6 runs/day during training (inter-trial interval 30 sec, inter-run interval 60 sec).

Aged rats were treated twice daily with 0.001 mg/kg i.p. AGN 2979 (injected at 8.00 am and 8.00 pm). At least 6 rats were used in each treatment group.

The results are set forth in FIGS. IV and V.

I claim:

1. A method of enhancing memory or treating a patient suffering from cognitive deficiency, which comprises administering to the patient a memory enhancing amount of a compound of the following Formula I

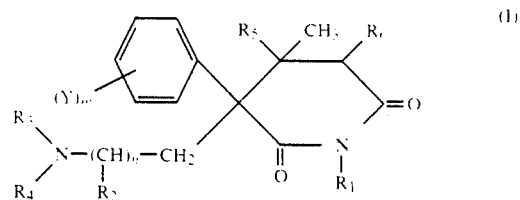

wherein:
$R_1$ represents hydrogen or $C_1$-$C_4$ alkyl;
n is 1 or 2;
$R_2$ represents hydrogen or methyl, provided that one $R_2$ is hydrogen when n is 2.
$R_3$ represents hydrogen or $C_1$-$C_2$ alkyl;
$R_4$ represents $C_1$-$C_2$ alkyl;
$R_5$ and $R_6$ independently represent hydrogen or methyl;
m is 0 to 3; and
each Y is in a meta or para position and independently represents hydroxy, $C_1$-$C_2$ alkoxy, $C_1$-$C_2$ alkyl, $C_1$-$C_2$ hydroxyalkyl, halogen, or trifluoromethyl, provided that hydroxy and alkoxy are not in the para position.

or a pharmacologically acceptable salt thereof as the sale active ingredient.

2. A method as claimed in claim 1, wherein the compound has the following Formula IA.

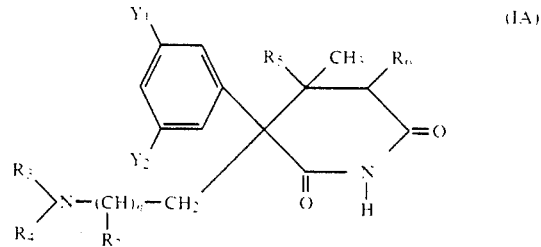

wherein:
n is 1 or 2;
$R_2$ represents hydrogen or methyl, provided that one $R_2$ is hydrogen when n is 2;
$R_3$ represents hydrogen or $C_1$-$C_2$ alkyl;
$R_4$ represents $C_1$-$C_2$ alkyl;
$R_5$ and $R_6$ independently represent hydrogen or methyl; and
$Y_1$ and $Y_2$ independently represent hydrogen, hydroxy or $C_1$-$C_2$ alkoxy, or a pharmacologically acceptable salt thereof.

3. A method as claimed in claim 2, wherein the compound has the following Formula IB.

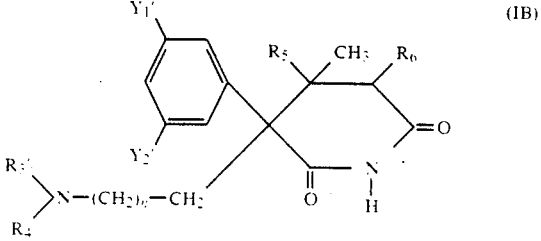

wherein:

n is 1 or 2;

$R_3'$ and $R_4$ independently represent $C_1$–$C_2$ alkyl;

$R_5$ and $R_6$ independently represent hydrogen or methyl;

$Y_1'$ represents hydroxy or $C_1$–$C_2$ alkoxy; and $Y_2'$ represents hydrogen, hydroxy or $C_1$–$C_2$ alkoxy, or a pharmacologically acceptable salt thereof.

4. A method as claimed in claim 3, wherein the compound is 3-(3'-methoxyphenyl)-3-(3''-N,N-dimethylaminopropyl)-4,4-dimethyl-2,6-dioxopiperidine.

5. A method as claimed in claim 4, wherein the compound is the minus isomer.

6. A method as claimed in claim 1, wherein the said memory enhancing amount is $10^{-5}$ to $10^2$ mg/kg.

7. A method as claimed in claim 6, wherein the said memory enhancing amount is $10^{-4}$ to $10^2$ mg/kg.

8. A method as claimed in claim 1, wherein the compound of Formula I is administered in unit dosage form containing $10^{-4}$ to $10^2$ mg of the said compound.

9. A method as claimed in claim 8, wherein the unit dosage form contains $10^{-3}$ to $10^{-1}$ mg of the said compound.

* * * * *